United States Patent [19]

Manolas et al.

[11] Patent Number: 5,741,553
[45] Date of Patent: Apr. 21, 1998

[54] PET REPELLANTS

[75] Inventors: John A. Manolas, Lake Forest; Brian D. Olms, Willow Springs, both of Ill.

[73] Assignee: Venus Laboratories, Incorporated, Wood Dale, Ill.

[21] Appl. No.: 485,684

[22] Filed: Jun. 7, 1995

[51] Int. Cl.$^6$ ........................... A01N 25/02; A01N 31/00
[52] U.S. Cl. ............. 427/421; 427/384; 427/394; 106/15; 106/18.32; 424/10.31; 424/10.4; 424/405; 514/920
[58] Field of Search ................. 514/920; 424/10.4, 424/405, 10.31; 106/15, 18.32; 427/421, 384, 394

[56] References Cited

U.S. PATENT DOCUMENTS

| | | | |
|---|---|---|---|
| 3,923,997 | 12/1975 | Meuly | 424/45 |
| 3,935,137 | 1/1976 | Minkoff | 523/103 |
| 4,005,038 | 1/1977 | Minkoff | 523/103 |
| 4,064,316 | 12/1977 | Curtis | 428/522 |
| 4,438,090 | 3/1984 | Brite | 424/10.31 |
| 4,461,758 | 7/1984 | Brite | 424/10.31 |
| 4,661,504 | 4/1987 | Hollander et al. | 514/373 |
| 4,818,535 | 4/1989 | Baines et al. | 424/409 |
| 4,853,413 | 8/1989 | Katz et al. | 514/526 |
| 4,940,583 | 7/1990 | Thompson | 424/195.1 |
| 5,142,817 | 9/1992 | Rolf | 47/24 |
| 5,224,967 | 7/1993 | Rolf et al. | 47/58 |
| 5,364,626 | 11/1994 | Hasegawa et al. | 424/403 |
| 5,464,625 | 11/1995 | Nolte et al. | 424/405 |
| 5,478,487 | 12/1995 | Hurme | 252/70 |

FOREIGN PATENT DOCUMENTS

| | | |
|---|---|---|
| 2254807 | 10/1992 | United Kingdom . |
| 94/04027 | 3/1994 | WIPO . |

OTHER PUBLICATIONS

Photocopy of front and back of Pet Sense Bitter Spray product, Revere Manufacturing No Date.
Photocopy of front and back of Outright Habit Breaker product, The Bramton Company, ©1992 No Month.
Copy of Revere Manufacturing invoice showing first sale of Pet Sense Bitter Spray (Aug. 15, 1995).

*Primary Examiner*—Anthony Green
*Attorney, Agent, or Firm*—Wallenstein & Wagner, Ltd.

[57] ABSTRACT

A pet repellant for use on furniture, rugs, upholstery and other water-safe surfaces to deter household pets from chewing, licking, scratching and urinating on the above mentioned surfaces. More particularly, the present invention relates to a non-volatile, odorless pet repellant that will remain on a surface to which it is applied for extended periods of time. Specifically, the pet repellant of the present invention comprises from about 0.005% by weight to about 0.06% by weight bittering agent, from about 0.01% by weight to about 1.0% by weight preservative, and from about 0.0001% by weight to about 0.01% by weight non-staining color. The pet repellant also contains a carrier, such as water.

25 Claims, No Drawings

PET REPELLANTS

FIELD OF THE INVENTION

The present invention generally relates to pet repellants. Particularly, the present invention relates to pet repellants that deter animals from chewing, licking, scratching and urinating on treated surfaces. More particularly, the present invention relates to non-volatile, odorless pet repellants that will remain on a surface to which it is applied for extended periods of time.

BACKGROUND OF THE INVENTION

A common problem which arises with household pets is that there is a tendency for these pets to urinate indoors on furniture, rugs, and upholstery, as well as on other surfaces. Additionally, some pets go through periods of teething, chewing, and clawing which could result in a great deal of damage to the owner's property.

Existing pet repellant products are typically based on volatile ingredients that evaporate at a fairly substantial rate. Therefore, these products tend to lose their effectiveness in a relatively short period of time, some as fast as half of a day. To be effective, the consumer must reapply the product on a frequent, regular basis.

Therefore, needs exist to improve pet repellants. Particularly, needs exist to improve the effectiveness of pet repellants to be useful for extended periods of time without the need to reapply the product on a frequent, regular basis. The present invention satisfies these and other needs to improve pet repellants.

Other aspects and advantages of the present invention will become apparent after reading this disclosure, including the Claims, and reviewing the accompanying drawings.

SUMMARY OF THE INVENTION

The present invention provides a non-volatile pet repellant that deters pets from chewing, licking, scratching and urinating on surfaces. The deterrence effect of the pet repellant is primarily the result of a bittering agent. The present pet repellant invention is non-staining, and can be used on any surface that is not harmed by water. The pet repellant is also totally odorless to humans. Generally, the pet repellant is used indoors on furniture, rugs, upholstery and other water-safe surfaces, for example. The repellant may also be used outdoors. As the water in the pet repellant evaporates, a non-volatile residue remains. The residue is extremely bitter, and is effective because it remains on the surface for extended periods of time.

DETAILED DESCRIPTION OF THE INVENTION

Although the present invention can be made in many different forms, the preferred embodiments are described in this disclosure. This disclosure exemplifies the principles of the present invention and does not limit the broad aspects of the invention only to the illustrated embodiments.

All percentages of components given herein are weight percentages of the repellant, unless otherwise indicated.

The pet repellant of the present invention comprises from about 0.005% by weight to about 0.06% by weight bittering agent. The pet repellant also contains a carrier, such as water, to form 100% of the composition. The pet repellant may also contain from about 0.01% by weight to about 1.0% by weight preservative, and from about 0.0001% by weight to about 0.01% by weight non-staining dye.

The pet repellant of the present invention contains a bittering agent in a range of from about 0.005% by weight to about 0.06% by weight of the pet repellant. The preferred bittering agent is Denatonium Benzoate NF-Anhydrous. Bitrex®, manufactured by Henley Chemicals, Inc., is one form of Denatonium Benzoate NF-Anhydrous. The preferred amount of bittering agent is about 0.03% by weight of the pet repellant.

The remainder of the composition of the pet repellant comprises a carrier. Suitable carriers include tap water, filtered water, softened water and de-ionized water.

Optionally, the pet repellant of the present invention also contains a preservative in an amount of from about 0.01% by weight to about 1.0% by weight of the pet repellant. The preferred preservative is DMDM Hydantoin (55% solution) (CTFA name), otherwise known as 1,3-Dihydroxymethyl-5,5-dimethylhydantoin or 1,3-Dihydroxymethyl-2,4-imidazolidinedione. One property of the DMDM Hydantoin preservative is that it is water soluble. Glydant Microbial, manufactured by Lonza, is one form of this preservative. Other suitable preservatives include sodium benzoate, formalin, parabens, and quaternary ammonium compounds, for example. Parabens is a trade name for the methyl, propyl, butyl, and ethyl esters of p-hydroxybenzoic acid. The chemical names for these compounds are methyl-p-hydroxybenzoate, propyl-p-hydroxybenzoate and butyl-p-hydroxybenzoate. The preferred amount of preservative is about 0.1% by weight of the pet repellant.

Another optional component of the present invention includes a non-staining color dye in an amount of from about 0.0001% by weight to about 0.01% by weight of the pet repellant. Any non-staining color dye is suitable to give an appealing color to the product. An example of a suitable color dye includes Keyacid Blue GL, available from Keystone Aniline Corp. The preferred amount of non-staining color dye is about 0.001% by weight of the pet repellant.

A method of making a pet repellant in accordance with the principles of the present invention will now be described. First, the appropriate amounts of the repellant components are weighed to make a desired batch size, for example, a 300 gallon batch. Second, the proper amount of water is added to a cylindrical polyethylene tank. Next, the appropriate amounts of the pre-weighed Bitrex® (bittering agent), Glydant (preservative) and dye are added. The components can be added to the water in any order. The batch is mixed with a mixer that is powered by an electric motor at approximately 1750 RPM's.

One method for applying the pet repellant is to spray it lightly onto any water-safe surface. This can be accomplished in a number of different ways, including the use of a pump sprayer or trigger sprayer to apply the product. To be effective, approximately only 1–3 sprays is necessary to dampen the area lightly.

The preferred formula for the pet repellant of the present invention is as follows:

0.03% by weight Bitrex®;
0.1% by weight Glydant;
0.001% by weight dye; and
99.869% by weight water.

The preferred formula was tested on surfaces where pets were known to chew, claw, urinate or otherwise destroy the surface. Two separate types of tests were conducted using the preferred repellant formulation. In the first type of test, the pet's nose was lightly pushed into the fabric of the carpet or other material that had been sprayed with the pet repellant. In the second type of test, nothing was done to the pet after the surface had been sprayed. The results of the tests conducted according to both types of tests were overwhelmingly positive.

Regarding the first type of test, cats and dogs that had been clawing or urinating on a specific area stopped clawing or urinating on that area immediately after having their noses lightly pushed into the treated area. Further, the cats and dogs did not return to the treated area or re-soil the treated area for at least three weeks after a single treatment of the area. Some pets did not even claw or re-soil the treated area for more than two months after the single treatment. Cats that perpetually scratched sofas or other furniture stopped after having their noses lightly pushed into the areas treated with the repellant. All of the tests conducted according to the first test type produced positive results of repelling the pet.

Regarding tests conducted according to the second test type, most of the time the pet did not return to the treated area to claw or urinate. Observations of the pets indicated that generally, the pet did not return to claw or urinate in the treated area if the pet used his nose to find the area. Apparently, the pet's moist nose picks up some of the strong bittering agent residue, which causes a bittering sensation without the pet directly ingesting the residue through the pet's mouth. Also, in cases where the pet clawed at a treated area, the pet would lick its paws after clawing, be exposed to the bitter taste, and stop clawing in the treated area. Although the pet repellant was more effective when the pet's nose was lightly pushed into the treated area, in most instances, the pet did not return to the area to claw or urinate.

Additional samples of the present invention were also prepared and tested. The compositions of the additional samples are as follows:

| Sample 1 | Sample 2 |
| --- | --- |
| 0.005% by weight Bitrex ® | 0.06% by weight Bitrex ® |
| 0.01% by weight Glydant | 1.0% by weight Glydant |
| 0.0001% by weight dye | 0.01% by weight dye |
| 99.9849% by weight water | 99.93% by weight water |

The results of the tests conducted with Sample 2 were equally as good as the results of the tests conducted with the preferred formula. The Sample 1 formulation was effective at keeping the pets from returning to the treated area. However, as expected, Sample 1 was not quite as effective at keeping the pets away for as long a period of time as the preferred formula because Sample 1 contains a lower amount of the bittering agent.

Although the pet repellant is odorless to humans, it is unclear whether it is odorless to pets as well. It is conceivable that the pet repellant causes an undesirable odor to the pet, thereby preventing the pet from approaching a particular area. Regardless, the strong, bitter taste of the pet repellant dissuades the pet from licking or chewing on an article that has been treated by the pet repellant. Additionally, most pets' noses are moist so a pet's nose picks up some of the strong bittering agent residue when the nose contacts the treated surface. In cases where the pet clawed at a treated area, the pet would lick its paws after clawing, be exposed to the bitter taste, and stop clawing in the treated area. Accordingly, the pet repellant causes a bittering sensation when the pet directly ingests the residue and when the residue contacts the pet's nose.

While the preferred embodiments have been illustrated and described, numerous changes and modifications can be made without significantly departing from the spirit and scope of this invention. Therefore, the inventors intend that such changes and modifications be covered by the appended Claims.

What is claimed:

1. A pet repellant consisting essentially of:
   a. from about 0.03% by weight to about 0.06% by weight denatonium benzoate bittering agent; and
   b. a water carrier present in an amount greater than 0% by weight up to about 99.97% by weight of the pet repellant.

2. The pet repellant of claim 1 further comprising from about 0.01% by weight to about 1.0% by weight preservative.

3. The pet repellant of claim 2 wherein the preservative is in an amount of about 0.1% by weight of the pet repellant.

4. The pet repellant of claim 2 wherein the preservative is selected from the group consisting of 1,3-Dihydroxymethyl-5,5-dimethylhydantoin; 1,3-Dihydroxymethyl-2,4-imidazolidinedione; sodium benzoate; formalin; methyl-p-hydroxybenzoate, propyl-p-hydroxybenzoate and butyl-p-hydroxybenzoate; and quaternary ammonium compounds.

5. The pet repellant of claim 4 wherein the preservative is in an amount of about 0.1% by weight of the pet repellant.

6. The pet repellant of claim 1 wherein the carrier comprises tap water, filtered water, softened water, de-ionized water or mixtures thereof.

7. A pet repellant comprising:
   a. from about 0.03% by weight to about 0.06% by weight denatonium benzoate bittering agent;
   b. a water carrier up to about 99.97% by weight of the pet repellant; and
   c. from about 0.0001% by weight to about 0.01% by weight non-staining color dye.

8. The pet repellant of claim 7 wherein the dye is in an amount of about 0.001% by weight of the pet repellant.

9. A pet repellant consisting essentially of:
   a. about 0.03 parts by weight denatonium benzoate bittering agent;
   b. about 0.1 parts by weight preservative;
   c. about 0.001 parts by weight non-staining color dye; and
   d. about 99.869 parts by weight water carrier.

10. The pet repellant of claim 9 wherein the preservative is selected from the group consisting of 1,3-Dihydroxymethyl-5,5-dimethylhydantoin; 1,3-Dihydroxymethyl-2,4-imidazolidinedione; sodium benzoate; formalin; methyl-p-hydroxybenzoate, propyl-p-hydroxybenzoate and butyl-p-hydroxybenzoate; and quaternary ammonium compounds.

11. The pet repellant of claim 10 wherein the carrier comprises tap water, filtered water, softened water, de-ionized water or mixtures thereof.

12. A method of repelling an animal comprising the steps of:

providing a pet repellant comprising:
   a. from about 0.005% by weight to about 0.06% by weight denatonium benzoate bittering agent; and
   b. a water carrier from about 99.94% by weight to about 99.995% by weight of the pet repellant;

applying the repellant to a surface to produce a treated surface; and, exposing the animal to the treated surface.

13. The method of repelling an animal of claim 12 wherein the exposing step further comprises the step of contacting a nose of the animal with the repellant.

14. The method of repelling an animal of claim 13 wherein the contacting step further comprises the step of pushing the nose against the treated surface.

15. The method of repelling an animal of claim 12 wherein the exposing step further comprises the step of contacting a mouth of the animal with the repellant.

16. The method of repelling an animal of claim 15 wherein the contacting a mouth step comprises the steps of contacting a portion of the animal other than the mouth with the repellant to produce a treated portion of the animal; and, subsequently contacting the mouth with the treated portion of the animal.

17. The method of repelling an animal of claim 12 further comprising, after the applying step and before the exposing step, the step of permitting the carrier to evaporate off of the treated surface while the bittering agent remains on the treated surface.

18. The method of repelling an animal of claim 17 further comprising the step of reapplying the repellant to the treated surface after the exposed animal has been repelled from the treated surface for at least three weeks.

19. The method of repelling an animal of claim 12 wherein the applying step comprises the step of applying the repellant to a surface selected from the group consisting of furniture, rugs, and upholstery.

20. The method of repelling an animal of claim 12 wherein the applying step comprises the step of spraying the repellant onto the surface.

21. The method of repelling an animal of claim 12 further comprising the step of reapplying the repellant to the treated surface after the exposed animal has been repelled from the treated surface for at least three weeks.

22. The method of repelling an animal of claim 12 wherein the denatonium benzoate is present in an amount of greater than 0.012% by weight of the solution to about 0.06% by weight of the solution.

23. The method of repelling an animal of claim 22 wherein the step of applying the repellant to a surface includes applying the repellant to a surface other than a surface on the animal to be repelled.

24. The method of repelling an animal of claim 22 wherein the denatonium benzoate bittering agent is present in an amount of greater than 0.025% by weight of the solution.

25. The method of repelling an animal of claim 24 wherein the step of applying the repellant to a surface includes applying the repellant to a surface other than a surface on the animal to be repelled.

* * * * *

UNITED STATES PATENT AND TRADEMARK OFFICE
CERTIFICATE OF CORRECTION

PATENT NO. : 5,741,553
DATED : April 21, 1998
INVENTOR(S) : Manolas et al.

It is certified that error appears in the above-identified patent and that said Letters Patent is hereby corrected as shown below:

Column 6, Line 9, after "denatonium benzoate" insert --bittering agent--.

Signed and Sealed this

Fourteenth Day of July, 1998

Attest:

BRUCE LEHMAN

Attesting Officer

Commissioner of Patents and Trademarks